(12) United States Patent
Ogawa et al.

(10) Patent No.: US 11,324,728 B2
(45) Date of Patent: May 10, 2022

(54) DOSING REGIMENS FOR THE TREATMENT OF FUNGAL INFECTIONS

(71) Applicant: Seren Pharmaceuticals Inc., Tokyo (JP)

(72) Inventors: Osamu Ogawa, Tokyo (JP); Hideyo Yamaguchi, Tokyo (JP)

(73) Assignee: Seren Pharmaceuticals Inc., Tokyo (JP)

( * ) Notice: Subject to any disclaimer, the term of this patent is extended or adjusted under 35 U.S.C. 154(b) by 0 days.

(21) Appl. No.: 16/763,425

(22) PCT Filed: Nov. 28, 2018

(86) PCT No.: PCT/IB2018/059418
§ 371 (c)(1),
(2) Date: May 12, 2020

(87) PCT Pub. No.: WO2019/106571
PCT Pub. Date: Jun. 6, 2019

(65) Prior Publication Data
US 2020/0316033 A1    Oct. 8, 2020

Related U.S. Application Data

(60) Provisional application No. 62/591,445, filed on Nov. 28, 2017.

(51) Int. Cl.
*A61K 31/427* (2006.01)
*A61K 31/675* (2006.01)
*A61P 31/10* (2006.01)
*A61K 9/00* (2006.01)

(52) U.S. Cl.
CPC .......... *A61K 31/427* (2013.01); *A61K 31/675* (2013.01); *A61P 31/10* (2018.01); *A61K 9/0053* (2013.01)

(58) Field of Classification Search
CPC .. A61K 31/427; A61K 31/675; A61K 9/0053; A61P 31/10; A61P 43/00
See application file for complete search history.

(56) References Cited

U.S. PATENT DOCUMENTS

2006/0264406 A1   11/2006   Gao et al.
2010/0249426 A1    9/2010   Ishimoto et al.
2015/0118299 A1    4/2015   Ueki

OTHER PUBLICATIONS

Yamaguchi, H., "Potential of Ravuconazole and its Prodrugs as the New Oral Therapeutics for Onychomycosis", Med. Mycol. J., 2016, pp. E93-E110, vol. 57E.

Gupta, A.K. et al., "A phase I/II randomized, double-blind, placebo-controlled, dose ranging study evaluating the efficacy, safety and pharmacokinetics of ravuconazole in the treatment of onychomycosis", JEADV, 2005, pp. 437-443 vol. 19, issue No. 4.

Watanabe, S. et.al., "Evaluation of the New Oral Antifungul Agent Fosravuconazole in Patients with Onychomycosos; A Multicenter, Dose-Finding Study, The Nishinihon Journal of Dermatology", Oct. 1, 2018, pp. 470-478, vol. 80, issue No. 5, (English Language Abstract Included).

Watanabe, S. et.al., "Efficacy and safety of fosravuconazole L-Lysine ethanolate, a novel oral triazole antifungal agent, for the treatment of onychomycosis: A Multicenter, double-blind, randmized phase III study", The Journal of dermatology, Aug. 29, 2018, pp. 1151-1159, vol. 45, issue No. 10.

Written Opinion dated Mar. 12, 2019 in International Application No. PCT/IB2018/059418.

International Search Report dated Mar. 12, 2019 in International Application No. PCT/IB2018/059418.

*Primary Examiner* — Sarah Pihonak
*Assistant Examiner* — Jason Deck
(74) *Attorney, Agent, or Firm* — Kim IP Law Group LLC

(57) ABSTRACT

Described herein are dosing regimens for the treatment of fungal infections such as onychomycosis using ravuconazole or a salt, solvate or prodrug thereof.

15 Claims, 5 Drawing Sheets

DOSING REGIMENS FOR THE TREATMENT OF FUNGAL INFECTIONS

CROSS-REFERENCE TO RELATED APPLICATIONS

This application is a U.S. national phase application under 35 U.S.C. § 371 of International Application No. PCT/IB2018/059418, filed on Nov. 28, 2018, which claims priority to U.S. Provisional Patent Application No. 62/591,445, filed Nov. 28, 2017, the disclosures of each of which hereby being incorporated by reference in their entirety for all purposes.

TECHNICAL FIELD

Principles and embodiments of the present invention relate generally to the treatment of fungal infections using azoles such as ravuconazole and its prodrugs.

BACKGROUND

Fungal infections, also known as mycoses, are common infections in animals that can range in severity and invasiveness. Fungal infections are typically classified as being superficial, cutaneous, subcutaneous, or systemic. Most fungal infections are not life-threatening, but these infections can negatively impact the patient's quality of life.

Onychomycosis, also known as tinea unguium, is an example of a common fungal infection, particularly in elderly patients and those with compromised immune systems. Onychomycosis is a fungal infection of the nail can be caused by many different types of fungi, including yeasts, dermatophytes and molds. Members of the genuses *Candida*, *Aspergillus* and *Trichophyton* are common causes for onychomycosis in humans. Onychomycosis can affect both toenails and fingernails, but toenail infections are more common.

Current treatments for fungal infections such as onychomycosis include griseofulvin, terbinafine, fluconazole and itraconazole. However, these existing therapies suffer from low clinical and mycological cure rates, high recurrence rates, and potential adverse events. Accordingly, there is a need for new therapies for the treatment of fungal infections such as onychomycosis.

SUMMARY

One aspect of the present invention pertains to a method of treating a fungal infection in a patient in need thereof, the method comprising administering to the patient a therapeutically effective dose of ravuconazole or a pharmaceutically acceptable salt, solvate or prodrug thereof. In various embodiments, the therapeutically effective dose is administered daily in an amount equivalent to about 50 mg to about 150 mg of ravuconazole.

In one or more embodiments, the fungal infection comprises one or more of onychomycosis, oral candidiasis, esophageal candidiasis, vaginal candidiasis, aspergillosis, sinusitis, otitis media or dermatophytosis.

In one or more embodiments, the fungal infection comprises toenail onychomycosis.

In one or more embodiments, the fungal infection is caused by one or more fungi selected from *Candida*, *Trichophyton Aspergillus*, *Malassezia* and/or *Cryptococcus*.

In one or more embodiments, the therapeutically effective dose is administered daily in an amount equivalent to about 75 mg to about 125 mg of ravuconazole.

In one or more embodiments, the therapeutically effective dose is administered daily in an amount equivalent to about 100 mg of ravuconazole.

In one or more embodiments, the prodrug is fosravuconazole or a pharmaceutically acceptable salt or solvate thereof.

In one or more embodiments, the prodrug is an L-lysine salt of fosravuconazole or a solvate thereof.

In one or more embodiments, the prodrug is fosravuconazole L-lysine ethanolate (1:1:1).

In one or more embodiments, the therapeutically effective dose is administered for at least 4 weeks.

In one or more embodiments, the therapeutically effective dose is administered orally.

Another aspect of the present invention pertains to a method of treating onychomycosis in a patient in need thereof, the method comprising administering to the patient a therapeutically effective dose of fosravuconazole or a pharmaceutically acceptable salt or solvate thereof. In various embodiments, the therapeutically effective dose is administered daily in an amount equivalent to about 50 mg to about 150 mg of ravuconazole.

In one or more embodiments, the onychomycosis comprises toenail onychomycosis.

In one or more embodiments, the onychomycosis is caused by one or more fungi selected from *Candida*, *Trichophyton Aspergillus*, *Malassezia* and/or *Cryptococcus*.

In one or more embodiments, the therapeutically effective dose is administered daily in an amount equivalent to about 75 mg to about 125 mg of ravuconazole.

In one or more embodiments, the therapeutically effective dose is administered daily in an amount equivalent to about 100 mg of ravuconazole.

In one or more embodiments, the pharmaceutically acceptable salt or solvate is an L-lysine salt or a solvate thereof.

In one or more embodiments, the solvate is fosravuconazole L-lysine ethanolate (1:1:1).

In one or more embodiments, the therapeutically effective dose is administered for at least 4 weeks.

Another aspect of the present invention pertains to a method of treating onychomycosis in a patient in need thereof, the method comprising orally administering to the patient a therapeutically effective dose of fosravuconazole L-lysine ethanolate (1:1:1), wherein the therapeutically effective dose is administered daily in an amount equivalent to about 100 mg of ravuconazole.

In one or more embodiments, the onychomycosis comprises toenail onychomycosis.

In one or more embodiments, the therapeutically effective dose is administered for at least 4 weeks.

BRIEF DESCRIPTION OF THE DRAWINGS

Further features of the present invention will become apparent from the following written description and the accompanying figures, in which.

DETAILED DESCRIPTION

Figure 1:
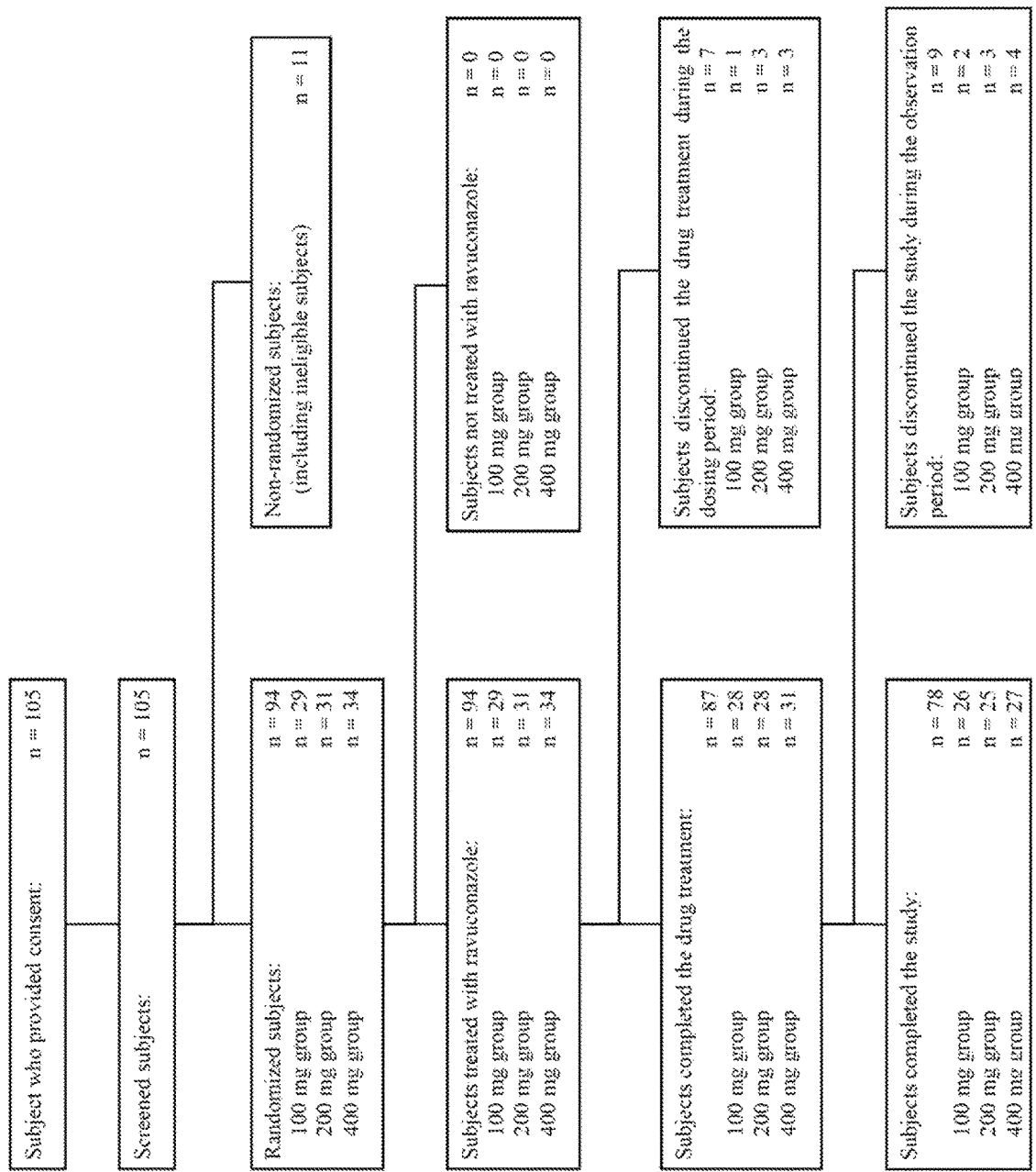
FIG. 1 shows the disposition of all subjects from a clinical trial investigating the use of fosravuconazole for the treatment of onychomycosis.

Before describing several exemplary embodiments of the invention, it is to be understood that the invention is not limited to the details of construction or process steps set forth in the following description. The invention is capable of other embodiments and of being practiced or being carried out in various ways.

Various embodiments of the present invention pertain to dosing regimens for the administration of ravuconazole, its salts, solvates and prodrugs, for the treatment of fungal infections. In one or more embodiments, the fungal infection comprises onychomycosis, such as toenail onychomycosis.

It has surprisingly been discovered that dosing regimens using less than 200 mg (ravuconazole equivalent) per day are effective in treating fungal infections such as onychomycosis. Previously, a Phase I/II dose ranging clinical study had found 200 mg of ravuconazole to be the most effective dosing regimen for treating onychomycosis. However, as described in more detail in Example 1 below, a daily dose of fosravuconazole equivalent to 100 mg of ravuconazole has now been found to have a high complete cure rate and a high mycological cure rate.

Ravuconazole, Salts, Solvates and Prodrugs

Ravuconazole, also known as 4-[2-[(2R,3R)-3-(2,4-difluorophenyl)-3-hydroxy-4-(1,2,4-triazol-1-yl)butan-2-yl]-1,3-thiazol-4-yl]benzonitrile or (2R,3R)-3-[4-(4-cyanophenyl)thiazol-2-yl]-2-(2,4-difluorophenyl)-1-(1H-1,2,4-triazol-1-yl)-butan-2-ol, is a triazole antifungal having the following structure:

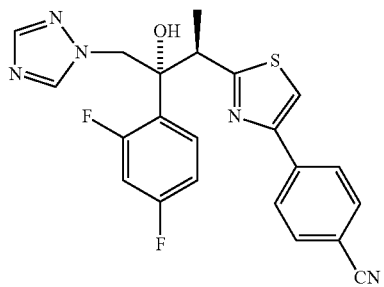 [SMILES: C[C@@H](c1nc(-c2ccc(C#N)cc2)cs1)[C@](O)(Cn1cncn1)c1ccc(F)cc1F]

Various prodrugs of ravuconazole are known. For example, U.S. Pat. Nos. 6,362,172 and 6,448,401 describe phosphate-containing prodrugs of triazole antifungal compounds such as ravuconazole, the disclosures of which are hereby incorporated by reference in their entirety.

Fosravuconazole, also known as 4-[2-[(1R,2R)-2-(2,4-difluorophenyl)-1-methyl-2-[(phosphonooxy)methoxy]-3-(1H-1,2,4-triazol-1-yl)propyl]-4-thiazolyl]benzo-nitrile or [(2R,3R)-3-[4-(4-cyanophenyl)-1,3-thiazol-2-yl]-2-(2,4-difluorophenyl)-1-(1,2,4-triazol-1-yl)butan-2-yl]oxymethyl dihydrogen phosphate, is a phosphonooxymethyl prodrug of ravuconazole having the following structure:

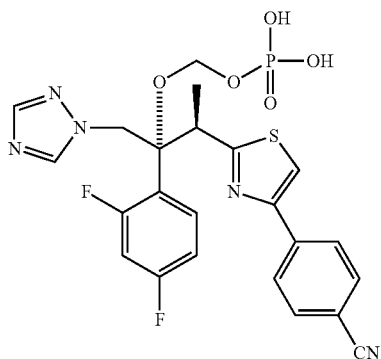 [SMILES: C[C@@H](c1nc(-c2ccc(C#N)cc2)cs1)[C@@](Cn1cncn1)(OCOP(=O)(O)O)c1ccc(F)cc1F]

Various salts and solvates of fosravuconazole have been previously described, such as monolysine and dilysine salts, as well as ethanol solvates of the monolysine salt. Examples of these salts and solvates can be found in U.S. Patent App. Pub. No. 2006/0264406, which is hereby incorporated by reference in its entirety. Other pharmaceutically acceptable salts and solvates of ravuconazole and fosravuconazole are also encompassed by the present disclosure.

In one or more embodiments, the solvate is fosravuconazole L-lysine ethanolate (1:1:1). The molecular formula of fosravuconazole L-lysine ethanolate (1:1:1) is $C_{23}H_{20}F_2N_5O_5PS \cdot C_6H_{14}N_2O_2 \cdot C_2H_6O$.

As fosravuconazole, its salts and solvates are prodrugs of ravuconazole, the doses of fosravuconazole are described herein as amounts equivalent to ravuconazole. Ravuconazole has a molecular weight of approximately 437.5 g/mol, fosravuconazole has a molecular weight of approximately 547.5 g/mol, and fosravuconazole L-lysine ethanolate (1:1:1) has a molecular weight of approximately 739.7 g/mol. Thus, 125.1 mg of fosravuconazole is equivalent to about 100 mg of ravuconazole. Similarly, an amount of fosravuconazole L-lysine ethanolate (1:1:1) that is equivalent to 100 mg of ravuconazole contains about 125.1 mg of fosravuconazole, about 33.4 mg of L-lysine and about 10.5 mg of ethanol. Other salts and solvates of ravuconazole and its prodrugs will have different conversion factors, depending on the molecular weight of the salt, solvate or prodrug.

Fungal Infections

Ravuconazole has broad antimicrobial activity covering a wide range of fungi, including most *Candida* and *Aspergillus* species, some non-*Aspergillus* species of filamentous fungi, *Cryptococcus*, dermatophytes (e.g. *Trichophyton* species), and fungi that cause the endemic mycoses.

In one or more embodiments, the fungal infection is caused by one or more species from the genuses *Candida, Aspergillus, Trichophyton, Malassezia* and/or *Cryptococcus*. Exemplary species include, but are not limited to, *Candida albicans, Candida krusei, Candida glabrata, Candida tropicalis, Candida parapsilosis, Cryptococcus neoformans, Malassezia furfur, Trichophyton mentagrophytes, Trichophyton rubrum* and/or *Aspergillus fumigatus*.

In one or more embodiments, the fungal infection is superficial, cutaneous, subcutaneous, or systemic. Affected areas can include, but are not limited to, skin, hair, nails, mucous membranes (e.g. oral, esophageal and vaginal), and/or the fungal infection can involve deeper tissues in the body.

In one or more embodiments, the ravuconazole, or salt, solvate or prodrug thereof (e.g. fosravuconazole), is used to treat a fungal infection such as onychomycosis, oral candidiasis, esophageal candidiasis, vaginal candidiasis, aspergillosis, sinusitis, otitis media or dermatophytosis.

In one or more embodiments, the fungal infection comprises onychomycosis, such as fingernail onychomycosis and/or toenail onychomycosis.

Dosing Regimens

In various embodiments, an effective amount of ravuconazole, or salt, solvate or prodrug thereof, is administered to a patient on a daily basis. In one or more embodiments, the effective amount of ravuconazole, or salt, solvate or prodrug thereof is equivalent to about 50 mg to about 150 mg of ravuconazole. Exemplary daily doses include amounts equivalent to about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg or about 150 mg of ravuconazole.

In one or more embodiments, the patient is administered about 50 mg to about 150 mg of ravuconazole per day, such as about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg or about 150 mg of ravuconazole per day.

In one or more embodiments, the patient is administered about 50 mg to about 150 mg of ravuconazole per day, provided as fosravuconazole or a salt or solvate thereof. In one or more embodiments, the effective amount is about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg or about 150 mg of ravuconazole per day, provided as fosravuconazole or a salt or solvate thereof.

In one or more embodiments, the patient is administered about 62.6 mg to about 187.7 mg of fosravuconazole per day, such as about 62.6 mg, about 68.8 mg, about 75.1 mg, about 81.3 mg, about 87.6 mg, about 93.8 mg, about 100.1 mg, about 106.3 mg, about 112.6 mg, about 118.8 mg, about 125.1 mg, about 131.4 mg, about 137.6 mg, about 143.9 mg, about 150.1 mg, about 156.4 mg, about 162.6 mg, about 168.9 mg, about 175.1 mg, about 181.4 mg or about 187.7 mg of fosravuconazole per day.

In one or more embodiments, the patient is administered about 62.6 mg to about 187.7 mg of fosravuconazole per day, provided as fosravuconazole L-lysine ethanolate (1:1:1). In one or more embodiments, the effective amount is about 62.6 mg, about 68.8 mg, about 75.1 mg, about 81.3 mg, about 87.6 mg, about 93.8 mg, about 100.1 mg, about 106.3 mg, about 112.6 mg, about 118.8 mg, about 125.1 mg, about 131.4 mg, about 137.6 mg, about 143.9 mg, about 150.1 mg, about 156.4 mg, about 162.6 mg, about 168.9 mg, about 175.1 mg, about 181.4 mg or about 187.7 mg of fosravuconazole per day, provided as fosravuconazole L-lysine ethanolate (1:1:1).

In one or more embodiments, the patient is administered about 84.5 mg to about 253.5 mg of fosravuconazole L-lysine ethanolate (1:1:1) per day, such as about 84.5 mg, about 93 mg, about 101.4 mg, about 109.9 mg, about 118.3 mg, about 126.8 mg, about 135.2 mg, about 143.7 mg, about 152.1 mg, about 160.6 mg, about 169 mg, about 177.5 mg, about 185.9 mg, about 194.4 mg, about 202.8 mg, about 211.3 mg, about 219.7 mg, about 228.2 mg, about 236.6 mg, about 245.1 mg or about 253.5 mg of fosravuconazole L-lysine ethanolate (1:1:1) per day.

In one or more embodiments, the ravuconazole, or salt, solvate or prodrug thereof (e.g. fosravuconazole), is administered for a certain treatment period. In one or more embodiments, the ravuconazole, or salt, solvate or prodrug thereof (e.g. fosravuconazole), is administered for at least 2 weeks, such as at least about 2, 3, 4, 5, 6, 7, 8, 9, 10, 11 or 12 weeks or at least about 1, 2, 3, 4, 5 or 6 months.

Formulation and Administration

The ravuconazole, or salt, solvate or prodrug thereof (e.g. fosravuconazole) can be administered to the patient via any suitable route. Exemplary routes of administration include oral, nasal, buccal, sublingual, topical, vaginal, rectal, intravenous and/or parenteral. In one or more embodiments, the ravuconazole, or salt, solvate or prodrug thereof (e.g. fosravuconazole) is administered to a patient orally.

Exemplary oral formulations for ravuconazole, fosravuconazole and related compounds are described in U.S. Patent App. Pub. Nos. 2010/0249426 and 2015/0118299, which are hereby incorporated by reference in their entirety.

In one or more embodiments, the patient is administered a tablet or capsule comprising 125.1 mg of fosravuconazole, 33.4 mg L-lysine, and 10.5 mg ethanol. Such tablet or capsule can also include excipients known in the art.

EXAMPLES

Example 1—Treatment of Onychomycosis

A Phase II clinical pharmacology study was conducted in subjects with onychomycosis of the toenail. The study investigated the pharmacokinetics, efficacy and safety of three different dosing regimens of fosravuconazole. Fosravuconazole was provided as fosravuconazole L-lysine ethanolate (1:1:1) in amounts equivalent to 100 mg, 200 mg or 400 mg of ravuconazole. The three treatment groups were as follows:

a. 100 mg group: fosravuconazole 100 mg (ravuconazole equivalent) once daily for 12 weeks;

b. 200 mg group: fosravuconazole 200 mg (ravuconazole equivalent) once daily for 7 days (then 21-day washout), 3 cycles c. 400 mg group: fosravuconazole 400 mg (ravuconazole equivalent) once daily for 7 days (then 21-day washout), 3 cycles The dosing regimens of administering 200 mg or 400 mg for 7 days (21-day washout), for 3 cycles, are referred to herein as 200 mg (pulse treatment) or 400 mg (pulse treatment), respectively.

Pharmacokinetic Endpoints

The pharmacokinetic endpoints were: (1) toenail ravuconazole concentrations at Week 12 after study treatment initiation and (2) changes over time in plasma and nail ravuconazole concentrations.

Efficacy Endpoints

The efficacy endpoints were: (1) overall clinical efficacy; (2) changes over time in efficacy; (3) confirmation of elements of dermatophytes by direct microscopy; and (4) results of identification of dermatophytes by the polymerase chain reaction (PCR) method.

Safety Endpoints

The safety endpoints were: (1) adverse events (AEs); (2) adverse reactions; and (3) laboratory tests.

Results

Disposition of Subjects

The disposition of subjects is shown in FIG. 1. Ravuconazole was given to 94 subjects and 7 subjects were discontinued from the study during the study treatment period and 9 subjects during the observation period.

A total of 7 subjects were discontinued from the study during the dosing period. The reason for discontinuation was "The investigator or subinvestigator determined that the continuation of the study was inappropriate for other reasons" in 3 subjects, "AST or ALT level was 2.5-fold or higher of the upper limit of normal (ULN) at the laboratory test institute" in 2 subjects, "subject was found to have not met the inclusion criteria or have met the exclusion criteria" in 1 subject, and "continuation of the study was judged inappropriate due to the onset of adverse events (AEs)" in 1 subject.

A total of 16 subjects were discontinued from the study during the entire study period. The most common reason for discontinuation was "Subject decided to prematurely terminate the study" in 7 subjects followed by "AST or ALT level was 2.5-fold or higher of the upper limit of normal (ULN) at the laboratory test institute" in 3 subjects" and "The investigator or subinvestigator determined that the continuation of the study was inappropriate for other reasons" in 3 subjects, respectively, and "subject was found to have not met the inclusion criteria or have met the exclusion criteria", "Continuation of the study was judged inappropriate based on the course of the primary disease or complications" and "continuation of the study was judged inappropriate due to the onset of adverse events (AEs)" in 1 subject, respectively.

Pharmacokinetic Results

Figure 2A:
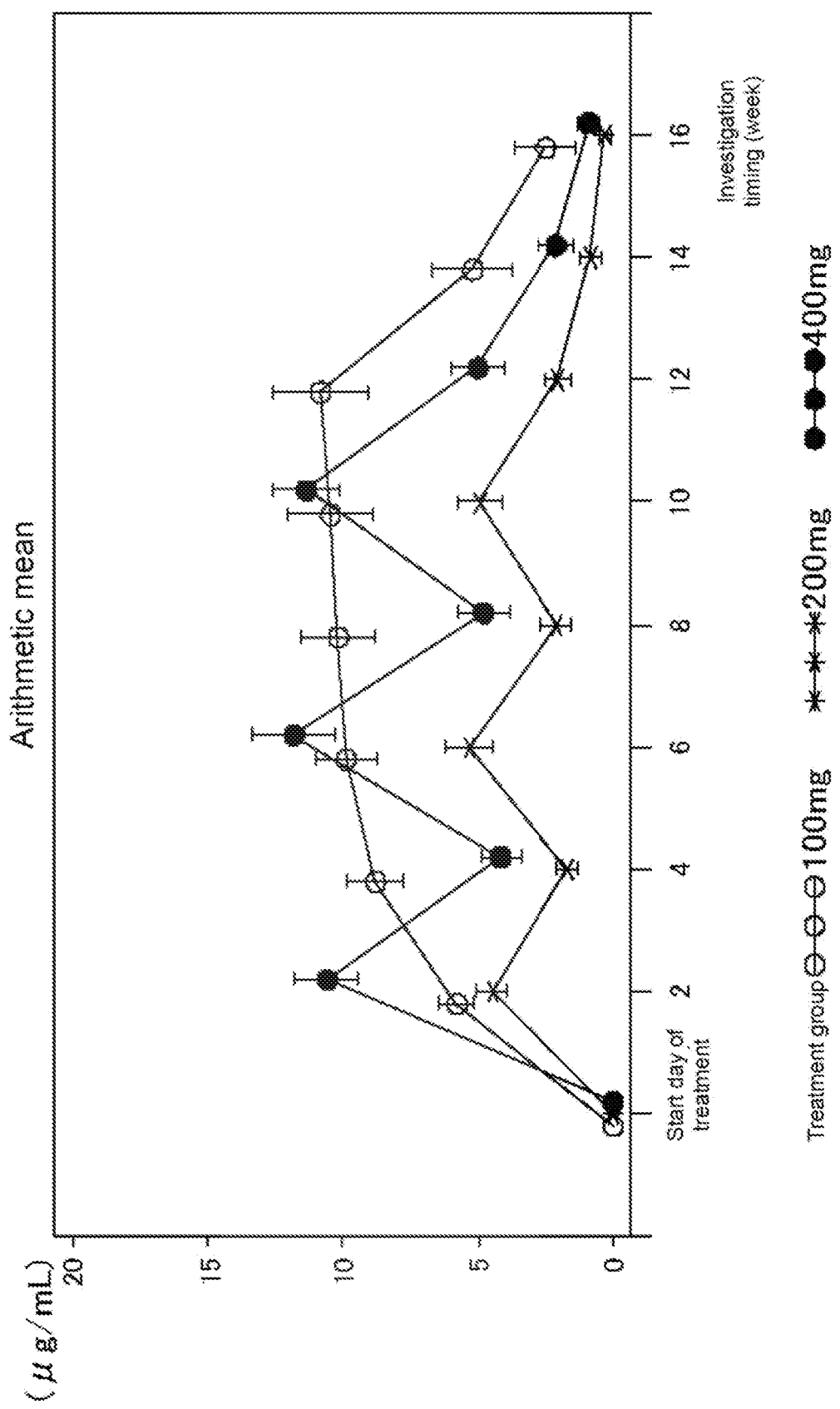
FIGS. 2A and 2B show the arithmetic mean and geometric mean, respectively, for plasma ravuconazole concentrations during a clinical trial investigating the use of fosravuconazole for the treatment of onychomycosis.
Figure 2B:
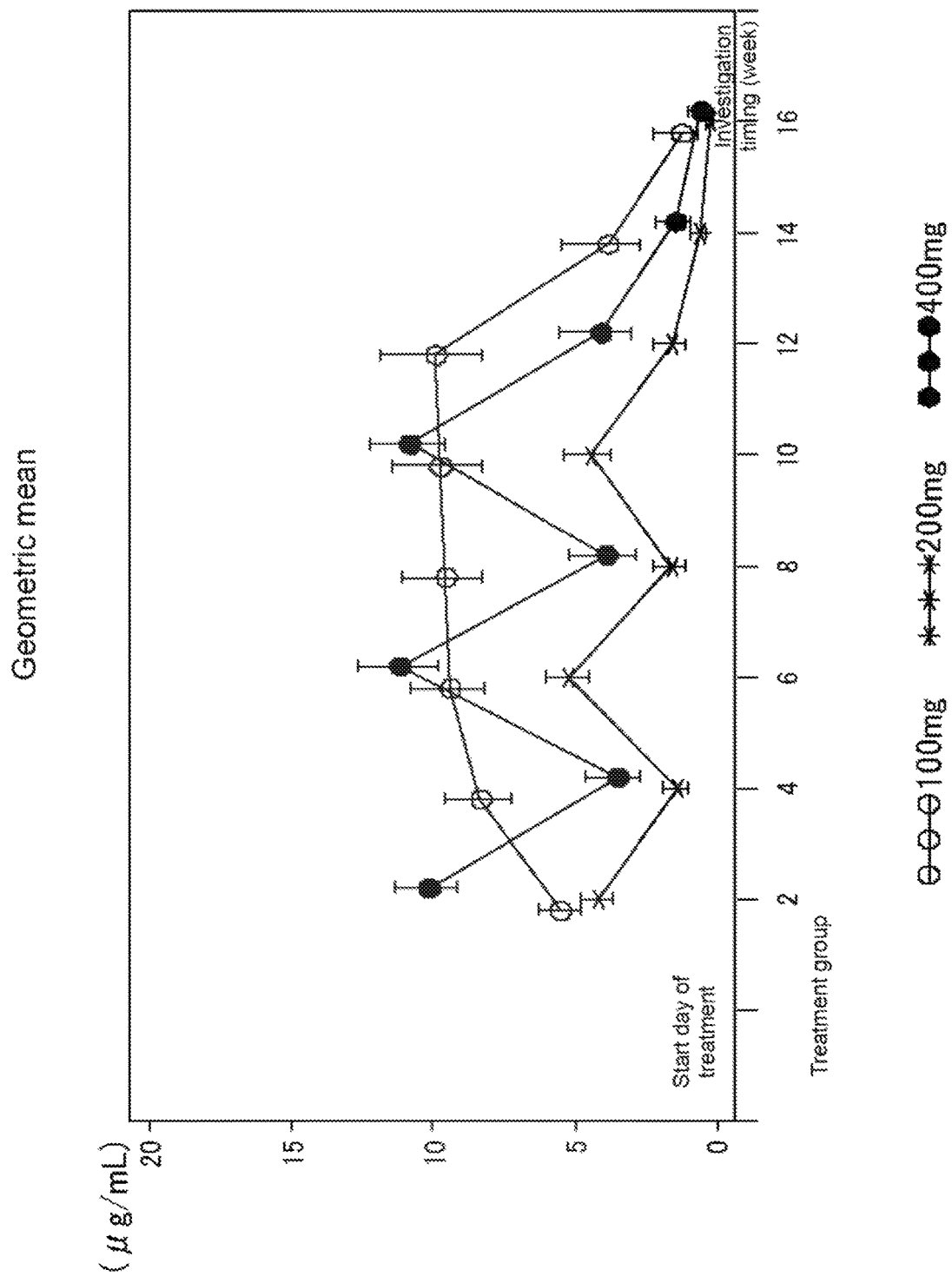
Figure 3A:
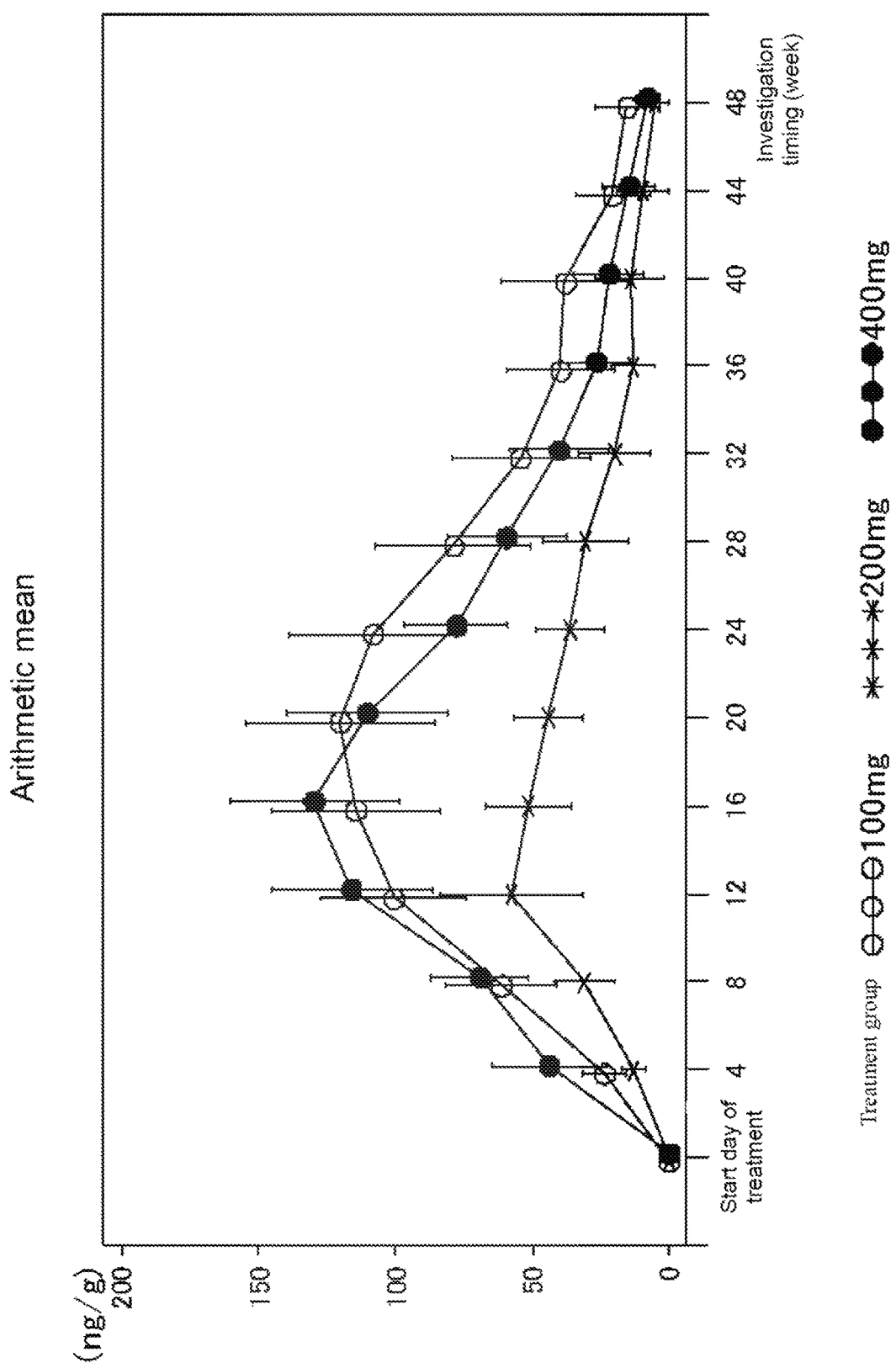
FIGS. 3A and 3B show the arithmetic mean and geometric mean, respectively, for toenail ravuconazole concentrations during a clinical trial investigating the use of fosravuconazole for the treatment of onychomycosis.
Figure 3B:
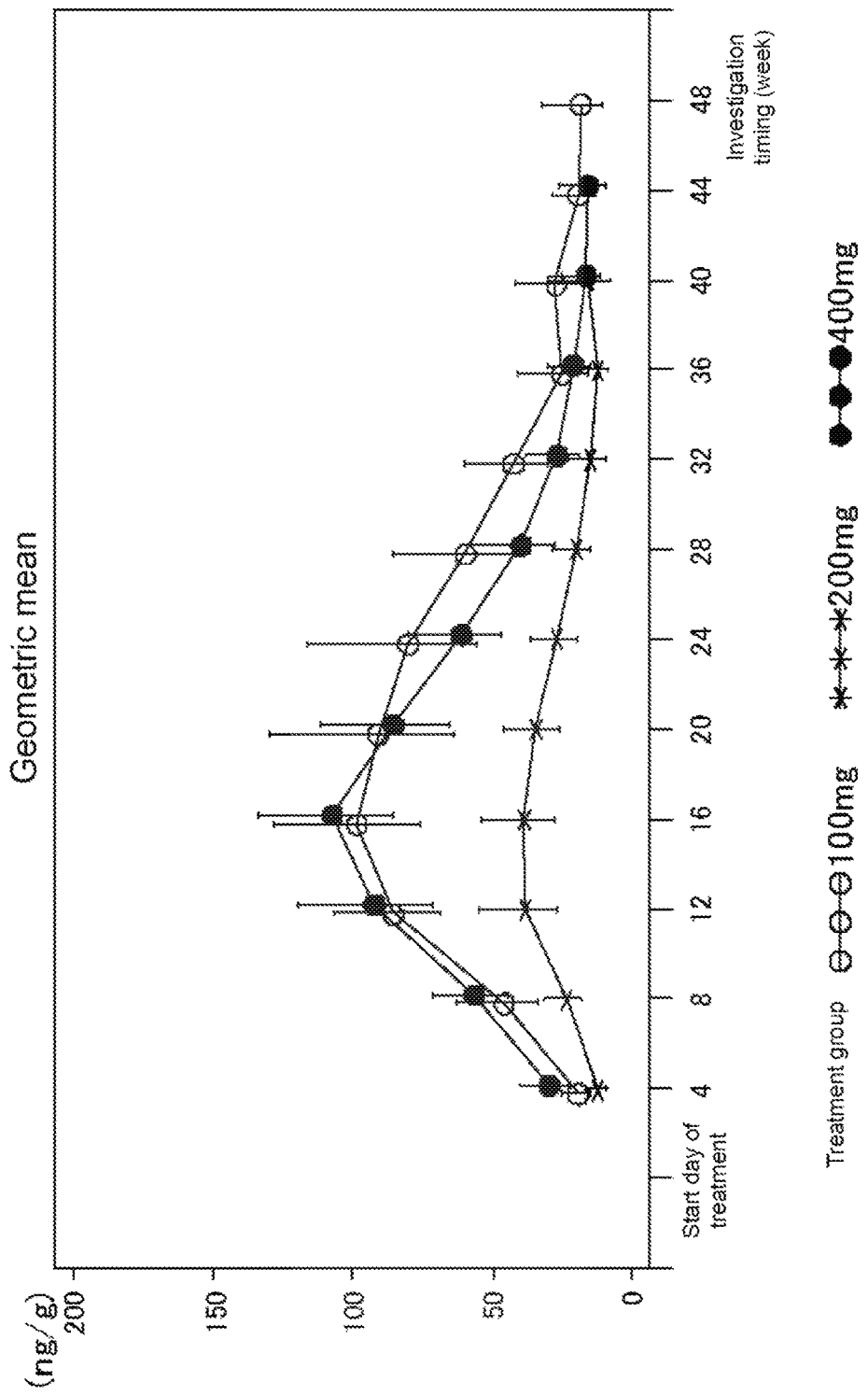

The arithmetic mean and geometric mean for plasma ravuconazole concentrations are shown in FIGS. 2A and 2B, respectively. Similarly, the arithmetic mean and geometric mean for toenail ravuconazole concentrations are shown in FIGS. 3A and 3B, respectively.

Both arithmetic mean and geometric mean for toenail ravuconazole concentrations in the 200 mg (pulse treatment) group did not exceed $MIC_{90}$ (60 ng/mL), which were inferior to the 100 mg (once daily dose) and 400 mg (pulse treatment) groups in terms of pharmacokinetics.

Toenail ravuconazole concentrations in the 100 mg (once daily dose) group exceeded $MIC_{90}$ in arithmetic mean at Week 8 and maintained at $MIC_{90}$ or higher until Week 28. Similarly, geometric mean toenail ravuconazole concentrations in the 100 mg (once daily dose) group exceeded $MIC_{90}$ at Week 12 after the study treatment initiation and maintained at $MIC_{90}$ or higher until Week 24.

Toenail ravuconazole concentrations in the 400 mg (pulse treatment) group exceeded $MIC_{90}$ in arithmetic mean at Week 8 after the study treatment initiation and maintained at $MIC_{90}$ or higher until Week 24. Similarly, geometric mean toenail ravuconazole concentrations in the 400 mg (pulse treatment) group exceeded $MIC_{90}$ at Week 12 after the study treatment initiation and maintained at $MIC_{90}$ or higher until Week 24.

Toenail ravuconazole concentrations in the 100 mg (once daily dose) group maintained at $MIC_{90}$ or higher for about 4 weeks longer than toenail ravuconazole concentrations in the 400 mg (pulse treatment) group.

Toenail ravuconazole concentrations in the 100 mg (once daily dose) group fluctuated at higher levels than toenail ravuconazole concentrations in the 400 mg (pulse treatment) group at Week 20 and onwards after the study treatment initiation.

Plasma ravuconazole concentrations in the 100 mg (once daily dose) group maintained at adjusted $MIC_{90}$ (3.00 μg/mL) or higher throughout the study treatment period.

Overall Clinical Efficacy

Overall clinical efficacy (cure rate and response rate) at Weeks 48 and 24 after the study treatment initiation for the efficacy analysis population (per protocol set, PPS) are presented in Tables 1 and 2 below. Overall clinical efficacy (cure rate and response rate) at Weeks 48 and 24 after the study treatment initiation for the full analysis set (FAS) are presented in Tables 3 and 4 below.

TABLE 1

Overall clinical evaluation at Week 48 after the study treatment initiation (efficacy analysis population: PPS)

| Treatment Group | Cured | Markedly improved | Improved | Slightly improved | Failed | Total | Cure rate* and 95% CI (%) | Response rate** and 95% CI (%) |
|---|---|---|---|---|---|---|---|---|
| 100 mg | 10 | 14 | 1 | 0 | 0 | 25 | 40.0 (21.2, 61.3) | 96.0 (79.7, 99.8) |
| 200 mg | 6 | 12 | 4 | 0 | 0 | 22 | 27.3 (10.8, 50.2) | 81.8 (59.8, 94.8) |
| 400 mg | 11 | 12 | 4 | 0 | 0 | 27 | 40.7 (22.4, 61.2) | 85.2 (66.3, 95.8) |

TABLE 2

Overall clinical evaluation at Week 24 after the study treatment initiation (efficacy analysis population: PPS)

| Treatment Group | Cured | Markedly improved | Improved | Slightly improved | Failed | Total | Cure rate* and 95% CI (%) | Response rate** and 95% CI (%) |
|---|---|---|---|---|---|---|---|---|
| 100 mg | 0 | 19 | 6 | 0 | 0 | 25 | 0.0 (0.0, 13.7) | 76.0 (54.9, 90.6) |
| 200 mg | 1 | 14 | 9 | 1 | 0 | 25 | 4.0 (0.2, 20.3) | 60.0 (38.7, 78.8) |
| 400 mg | 0 | 17 | 11 | 3 | 0 | 31 | 0.0 (0.0, 11.2) | 54.8 (36.1, 72.6) |

TABLE 3

Overall clinical evaluation at Week 48 after the study treatment initiation (full analysis set: FAS)

| Treatment Group | Cured | Markedly improved | Improved | Slightly improved | Failed | Total | Cure rate* and 95% CI (%) | Response rate** and 95% CI (%) |
|---|---|---|---|---|---|---|---|---|
| 100 mg | 10 | 15 | 1 | 0 | 0 | 26 | 38.5 (20.3, 59.4) | 96.2 (80.4, 99.9) |
| 200 mg | 8 | 13 | 4 | 0 | 0 | 25 | 32.0 (15.0, 53.5) | 84.0 (64.0, 95.4) |
| 400 mg | 11 | 12 | 4 | 0 | 0 | 27 | 40.7 (22.4, 61.2) | 85.2 (66.3, 95.8) |

TABLE 4

Overall clinical evaluation at Week 24 after the study treatment initiation (full analysis set: FAS)

| Treatment Group | Cured | Markedly improved | Improved | Slightly improved | Failed | Total | Cure rate* and 95% CI (%) | Response rate** and 95% CI (%) |
|---|---|---|---|---|---|---|---|---|
| 100 mg | 0 | 20 | 6 | 0 | 0 | 26 | 0.0 (0.0, 13.2) | 76.9 (56.4, 91.0) |
| 200 mg | 1 | 16 | 10 | 1 | 0 | 28 | 3.6 (0.1, 18.3) | 60.7 (40.6, 78.4) |
| 400 mg | 0 | 17 | 11 | 3 | 0 | 31 | 0.0 (0.0, 11.2) | 54.8 (36.1, 72.6) |

*Cure rate: Proportion of subjects evaluated as cured
**Response rate: Proportion of subjects evaluated as cured +markedly improved The criteria for assessment of overall clinical response are provided in Table 5 below:

TABLE 5

Criteria for assessment of Overall Clinical Response

| Assessment of overall clinical efficacy | Percent change in the area ratio for opacified nail plate | Direct microscopic result |
|---|---|---|
| Cured | No opacification | Negative |
| Markedly improved | ≥60% decrease | Any result |
| Improved | ≥30% and <60% decrease | Any result |
| Slightly improved | <30% decrease | Any result |
| Failed | No change or increase | Any result |

The cure rate in the 200 mg (pulse treatment) group was lower than that in the other groups in any analysis population. The cure rates in the 100 mg (once daily dose) and 400 mg (pulse treatment) groups were comparable. However, the response rate (cured+markedly improved) in the 100 mg (once daily dose) group of 96.0% was higher than the response rate of 85.2% in the 400 mg (pulse treatment) group.

Changes Over Time in Efficacy

The changes over time in the ratio for the turbidity area of the target nail are shown in Table 6 below:

TABLE 6

Changes in the turbidity area ratio regarding the target nail (PPS, %)

| Timing | Treatment Group | No. of Subjects | Mean | Standard Deviation | Minimum | Median | Maximum | 95% CI |
|---|---|---|---|---|---|---|---|---|
| Start day of treatment | 100 mg | 28 | 76.9 | 13.8 | 53 | 75.5 | 100 | (71.6, 82.2) |
| | 200 mg | 27 | 76.4 | 14.7 | 47 | 74.0 | 100 | (70.6, 82.1) |
| | 400 mg | 33 | 74.4 | 10.7 | 51 | 76.0 | 100 | (70.7, 78.2) |
| Week 4 | 100 mg | 28 | 72.9 | 15.6 | 40 | 72.0 | 100 | (66.9, 78.9) |
| | 200 mg | 27 | 69.6 | 16.9 | 44 | 70.0 | 100 | (62.9, 76.2) |
| | 400 mg | 33 | 66.9 | 13.0 | 46 | 67.0 | 92 | (62.4, 71.5) |
| Week 8 | 100 mg | 27 | 65.9 | 17.5 | 33 | 67.0 | 100 | (59.0, 72.8) |
| | 200 mg | 26 | 59.8 | 20.2 | 26 | 58.5 | 100 | (51.7, 67.9) |
| | 400 mg | 33 | 57.4 | 17.0 | 26 | 59.0 | 87 | (51.4, 63.4) |
| Week 12 | 100 mg | 27 | 55.6 | 13.9 | 34 | 56.0 | 84 | (50.2, 61.0) |
| | 200 mg | 25 | 51.4 | 20.7 | 9 | 49.0 | 89 | (42.9, 59.9) |
| | 400 mg | 31 | 49.3 | 17.0 | 19 | 52.0 | 84 | (43.1, 55.4) |
| Week 16 | 100 mg | 27 | 44.2 | 13.2 | 19 | 46.0 | 70 | (39.1, 49.4) |
| | 200 mg | 25 | 45.0 | 19.3 | 10 | 45.0 | 84 | (37.1, 52.9) |
| | 400 mg | 31 | 40.6 | 17.2 | 13 | 41.0 | 78 | (34.4, 46.9) |
| Week 20 | 100 mg | 25 | 34.6 | 11.5 | 10 | 36.0 | 57 | (29.9, 39.3) |
| | 200 mg | 25 | 35.8 | 19.0 | 0 | 34.0 | 74 | (28.0, 43.6) |
| | 400 mg | 31 | 31.1 | 15.2 | 8 | 29.0 | 73 | (25.6, 36.7) |
| Week 24 | 100 mg | 25 | 26.5 | 10.5 | 10 | 25.0 | 57 | (22.2, 30.7) |
| | 200 mg | 25 | 27.9 | 18.5 | 0 | 25.0 | 71 | (20.3, 35.5) |
| | 400 mg | 31 | 25.7 | 18.0 | 5 | 20.0 | 79 | (19.2, 32.3) |

TABLE 6-continued

Changes in the turbidity area ratio regarding the target nail (PPS, %)

| Timing | Treatment Group | No. of Subjects | Mean | Standard Deviation | Minimum | Median | Maximum | 95% CI |
|---|---|---|---|---|---|---|---|---|
| Week 28 | 100 mg | 25 | 19.4 | 9.0 | 3 | 18.0 | 44 | (15.7, 23.1) |
|  | 200 mg | 25 | 23.3 | 19.0 | 0 | 18.0 | 75 | (15.5, 31.1) |
|  | 400 mg | 27 | 18.3 | 13.3 | 0 | 16.0 | 46 | (13.1, 23.5) |
| Week 32 | 100 mg | 25 | 14.4 | 8.4 | 0 | 15.0 | 34 | (10.9, 17.8) |
|  | 200 mg | 25 | 20.0 | 18.8 | 0 | 9.0 | 72 | (12.3, 27.7) |
|  | 400 mg | 28 | 14.9 | 14.1 | 0 | 12.0 | 45 | (9.5, 20.3) |
| Week 36 | 100 mg | 25 | 12.0 | 9.3 | 0 | 9.0 | 33 | (8.2, 15.8) |
|  | 200 mg | 24 | 18.2 | 18.5 | 0 | 11.5 | 62 | (10.4, 25.9) |
|  | 400 mg | 27 | 13.5 | 13.3 | 0 | 9.0 | 42 | (8.3, 18.7) |
| Week 40 | 100 mg | 25 | 9.6 | 9.5 | 0 | 12.0 | 36 | (5.7, 13.5) |
|  | 200 mg | 23 | 16.0 | 15.6 | 0 | 10.0 | 47 | (9.3, 22.8) |
|  | 400 mg | 27 | 11.8 | 13.6 | 0 | 6.0 | 49 | (6.5, 17.1) |
| Week 44 | 100 mg | 25 | 8.6 | 9.6 | 0 | 8.0 | 39 | (4.7, 12.5) |
|  | 200 mg | 22 | 13.5 | 16.0 | 0 | 5.0 | 44 | (6.4, 20.6) |
|  | 400 mg | 27 | 11.9 | 14.6 | 0 | 6.0 | 45 | (6.2, 17.6) |
| Week 48 | 100 mg | 25 | 9.3 | 12.4 | 0 | 6.0 | 51 | (4.2, 14.4) |
|  | 200 mg | 22 | 14.6 | 15.7 | 0 | 9.0 | 46 | (7.7, 21.5) |
|  | 400 mg | 27 | 12.7 | 14.1 | 0 | 8.0 | 45 | (6.9, 18.4) |

As can be seen from Table 6, the mean ratio for the turbidity area of the target nail (Week 40 and onwards after the study treatment initiation) in the 100 mg (once daily dose) group was lower than that in the 200 mg (pulse treatment) of the 400 mg (pulse treatment) groups.

The clinical cure rate for the target nail at Week 48 after the study treatment initiation is shown in Table 7 below:

TABLE 7

Clinical cure rate for the target nail at Week 48 after the study treatment initiation (PPS, %)

| Treatment group | Clinical cure (no visual sign of infection) | Remaining of the visual sign of infection | Total | Clinical cure rate and 95% CI (%) |
|---|---|---|---|---|
| 100 mg group | 11 | 14 | 25 | 44.0 (24.5, 65.0) |
| 200 mg group | 7 | 15 | 25 | 31.8 (13.9, 54.8) |
| 300 mg group | 11 | 16 | 27 | 40.7 (22.4, 61.2) |

While relapse/reinfection occurred in 4 subjects in the 200 mg (pulse treatment) group and 1 subject in the 400 mg group, there was no subject in the 100 mg (once daily dose) group who had relapse/reinfection.

The response rates (cured+markedly improved) in the 100 mg (once daily dose) group (Weeks 24 and 48 after the study treatment initiation) were higher than those in the 400 mg (pulse treatment) group.

Mycological Cure (Results of Search for Fungal Elements by Direct Microscopy)

Presence or absence of fungal elements by direct microscopy at the each evaluation timing is shown in Table 8. At screening, fungal elements were found by direct microscopy in all treatment groups.

TABLE 8

Presence or absence of fungal elements by direct microscopy (PPS)

| Observation timing | Presence or absence of fungal elements | 100 mg group | 200 mg group | 400 mg group |
|---|---|---|---|---|
| At screening | Absence (%) | 0 (0.0) | 0 (0.0) | 0 (0.0) |
|  | Presence (%) | 28 (100.0) | 27 (100.0) | 33 (100.0) |
| Week 12 after the study treatment initiation | Absence (%) | 9 (33.3) | 13 (50.0) | 6 (19.4) |
|  | Presence (%) | 18 (16.7) | 13 (50.0) | 25 (80.6) |
| Week 24 after the study treatment initiation | Absence (%) | 12 (48.0) | 12 (48.0) | 14 (45.2) |
|  | Presence (%) | 13 (52.0) | 13 (52.0) | 17 (54.8) |
| Week 48 after the study treatment initiation | Absence (%) | 18 (72.0) | 8 (36.4) | 17 (63.0) |
|  | Presence (%) | 7 (28.0) | 14 (63.6) | 10 (37.0) |

As can be seen from Table 8, negative rate of fungal elements at Week 48 after the study treatment initiation was highest in the 100 mg (once daily dose) group followed by the 400 mg (pulse treatment) group and 200 mg (pulse treatment) group.

Disappearance rate of *Trichophyton rubrum*, which was frequently identified at patient screening, was highest in the 100 mg (once daily dose) group at 57.1%, followed by 52.1% for the 400 mg (pulse treatment) group and 36.8% for the 200 mg (pulse treatment) group.

Table 9 below shows the cure rate for various identified species:

TABLE 9

Overall clinical evaluation at Week 48 after the study

| Species | Treatment Group | Cured | Markedly improved | Improved | Slightly improved | Failed | Total | Cure rate* and 95% CI (%) |
|---|---|---|---|---|---|---|---|---|
| *Trichophyton rubrum* | 100 mg | 10 | 10 | 1 | 0 | 0 | 21 | 47.6 (25.8, 70.2) |
| | 200 mg | 6 | 11 | 2 | 0 | 0 | 19 | 31.6 (12.6, 56.5) |
| | 400 mg | 11 | 10 | 4 | 0 | 0 | 25 | 44.0 (24.5, 65.0) |
| *Trichophyton mentagrophytes* | 100 mg | 0 | 4 | 0 | 0 | 0 | 4 | 0.0 (0.0, 60.2) |
| | 200 mg | 0 | 0 | 2 | 0 | 0 | 2 | 0.0 (0.0, 84.1) |
| | 400 mg | 0 | 2 | 0 | 0 | 0 | 2 | 0.0 (0.0, 84.1) |
| *Trichophyton species* | 100 mg | — | — | — | — | — | — | — (-, -) |
| | 200 mg | 0 | 1 | 0 | 0 | 0 | 1 | 0.0 (0.0, 97.5) |
| | 400 mg | — | — | — | — | — | — | — (-, -) |

*Cure rate: Proportion of subjects evaluated as cured

As can be seen from Table 9, the cure rate of subjects infected with *Trichophyton rubrum* was higher in the 100 mg (pulse treatment) group than in the 400 mg (pulse treatment) group or the 200 mg (pulse treatment) group.

Safety Results

Patients treated with fosravuconazole were well-tolerated in all dosing groups.

The incidence of AEs was 89.7% in the 100 mg (once daily does) group, 64.5% in the 200 mg (pulse treatment) group, and 85.3% in the 400 mg (pulse treatment) group. There was no significant difference in AEs between the 100 mg (once daily dose) and 400 mg (pulse treatment) groups.

While tinea pedis occurred in 2 subjects in the 400 mg (pulse treatment) group, there was no new AE derived from fungal infection in the 100 mg (once daily dose) group).

No death or other serious AEs occurred in any of the treatment groups. AEs resulted in the discontinuation of the study treatment in 1 subject in the 100 mg (once daily dose) group and 4 subjects in the 400 mg (pulse treatment) group. Of the 4 subjects who discontinued the study treatment in the 400 mg (pulse treatment) group, the AEs were assessed as not related to the study drug in 2 subjects.

Moderate AEs occurred in 3 subjects in the 100 mg (once daily dose) group, 12 subjects in the 200 mg (pulse treatment) group, and 12 subjects in the 400 mg (pulse treatment) group. Thus, the number of moderate AEs was lowed in the 100 mg (once daily dose) group than either of the pulse treatment groups (200 mg or 400 mg).

As AEs with high incidences, γ-glutamyl transferase increased and liver function test abnormal were observed. In the detailed degree of changes in liver function test values, AST or ALT elevated to Grade 2 after the start of study treatment in 4 subjects in total; 2 subjects in the 100 mg (once daily dose) group, 1 subject in the 200 mg (pulse treatment) group, and 1 subject in the 400 mg (pulse treatment) group (Table 3.2-26, Table 3.2-27). Of the 4 subjects, AST or ALT increased after the completion of the study treatment in 2 subjects and either recovered or abated in the liver function test performed about 2 weeks later. Grade 2 AST or ALT increased recovered by discontinuing the study treatment in the other 2 subjects in the liver function test performed about 6 or 7 weeks later. In these 4 subjects, no other AEs suggesting liver disorder occurred.

CONCLUSIONS

The 100 mg (once daily dose) had the best overall results. The Week 48 cure rate for the 100 mg (once daily dose) group of 40.0% was comparable to the 400 mg (pulse treatment) group of 40.7%, and both were higher than the 27.3% cure rate for the 200 mg (pulse treatment) group. The 100 mg (once daily dose) group had a higher response rate at Week 48 of 96.0% than either the 200 mg (pulse treatment) group or the 400 mg (pulse treatment) groups, which were 81.8% and 85.2%, respectively.

The Week 48 mycological cure rate of 72.0% in the 100 mg (once daily dose) group was higher than either the 200 mg (pulse treatment) group or the 400 mg (pulse treatment) group, which were 36.4% and 63.0%, respectively. Moreover, the disappearance rate of fungal elements (*Trichophyton rubrum*) determined by a PCR method at Week 48 was 57.1% in the 100 mg (once daily dose) group, versus 52.0% in the 400 mg (pulse treatment) group and 36.8% in the 200 mg (pulse treatment) group.

The document attached as Appendix 1, entitled "Potential of Ravuconazole and its Prodrugs as the New Oral Therapeutics for Onychomycosis," is a review describing ravuconazole and its prodrugs as a potential oral treatment option for onychomycosis. Appendix 1 is incorporated by reference herein in its entirety.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A method of treating a fungal infection in a patient in need thereof, the method comprising orally administering to the patient a therapeutically effective dose of fosravuconazole L-lysine ethanolate (1:1:1), wherein the therapeutically effective dose is administered daily in an amount equivalent to about 50 mg to about 150 mg of ravuconazole.

2. The method of claim 1, wherein the fungal infection comprises one or more of onychomycosis, oral candidiasis, esophageal candidiasis, vaginal candidiasis, aspergillosis, sinusitis, otitis media or dermatophytosis.

3. The method of claim 1, wherein the fungal infection comprises toenail onychomycosis.

4. The method of claim 1, wherein the fungal infection is caused by one or more fungi selected from *Candida, Trichophyton, Aspergillus, Malassezia* or *Cryptococcus*.

5. The method of claim 1, wherein the therapeutically effective dose is administered daily in an amount equivalent to about 75 mg to about 125 mg of ravuconazole.

6. The method of claim 1, wherein the therapeutically effective dose is administered daily in an amount equivalent to about 100 mg of ravuconazole.

7. The method of claim 1, wherein the therapeutically effective dose is administered for at least 4 weeks.

8. The method of claim 1, wherein the fungal infection comprises onychomycosis.

9. The method of claim 8, wherein the onychomycosis is caused by one or more fungi selected from *Candida, Trichophyton, Aspergillus, Malassezia* or *Cryptococcus*.

10. The method of claim 8, wherein the therapeutically effective dose is administered daily in an amount equivalent to about 75 mg to about 125 mg of ravuconazole.

11. A method of treating onychomycosis in a patient in need thereof, the method comprising orally administering to the patient a therapeutically effective dose of fosravuconazole L-lysine ethanolate (1:1:1), wherein the therapeutically effective dose is administered daily in an amount equivalent to about 100 mg of ravuconazole.

12. The method of claim 11, wherein the onychomycosis comprises toenail onychomycosis.

13. The method of claim 11, wherein the therapeutically effective dose is administered for at least 4 weeks.

14. The method of claim 8, wherein the therapeutically effective dose is administered for at least 4 weeks.

15. The method of claim 12, wherein the therapeutically effective does is administered for at least 4 weeks.

* * * * *